United States Patent [19]

Watkinson

[11] Patent Number: 4,481,219

[45] Date of Patent: Nov. 6, 1984

[54] INHIBITION OF GROWTH IN FUNGI

[75] Inventor: Sarah C. Watkinson, Bladon, England

[73] Assignee: National Research Development Corporation, London, England

[21] Appl. No.: 395,928

[22] Filed: Jul. 7, 1982

[30] Foreign Application Priority Data

Jul. 16, 1981 [GB] United Kingdom ............... 8121918
Dec. 8, 1981 [GB] United Kingdom ............... 8136944

[51] Int. Cl.$^3$ ............................................. A01N 37/12
[52] U.S. Cl. .................................................. 424/319
[58] Field of Search ......................................... 424/319

[56] References Cited

U.S. PATENT DOCUMENTS 3,054,750  9/1962  Jolly ........................... 424/319
3,574,850  4/1971  Guillon ....................... 424/319
4,126,700  11/1978 Lover et al. ................. 424/319

FOREIGN PATENT DOCUMENTS 45-8873  3/1970  Japan ........................... 424/319

Primary Examiner—Douglas W. Robinson
Attorney, Agent, or Firm—Oblon, Fisher, Spivak, McClelland & Maier

[57] ABSTRACT

A composition, a concentrate of said composition and a method for inhibiting the growth of a fungus which is capable of growth over a non-nutrient surface which comprises treating the fungal mycelium or a foodbase on which the mycelium is capable of growing with a nitrogenous substance selected from those substances which are either translocated within the mycelium or taken up by the mycelium or both taken up and translocated and which are not utilized by the fungus for growth when said substance is the sole source of nitrogen supplied to the fungus.

35 Claims, No Drawings

INHIBITION OF GROWTH IN FUNGI

BACKGROUND OF THE INVENTION

This invention relates to the inhibition of growth in fungi and is particularly applicable to the control of the dry rot fungus.

Hitherto the eradication of dry rot has necessitated drastic treatment on the fabric of buildings containing the infestation because the fungus can grow extensively from a timber food base penetrating plaster and brickwork in order to reach further nutrient sources.

It has now been found that the growth of the dry rot fungus and other fungi at inaccessible sites in buildings can be inhibited by the application of certain substances to the exposed mycelium or food base. These and certain other substances are also of interest for the preservation of food bases from fungal infestation.

SUMMARY OF THE INVENTION

According to the present invention, a method for inhibiting the growth of a fungus which is capable of growth over a non-nutrient surface comprises treating the fungal mycelium or a food base on which the mycelium is capable of growing with a nitrogenous substance selected from those substances which are either translocated within the mycelium or taken up by the mycelium or both taken up and translocated and which are not utilised by the fungus for growth when said substance is the sole source of nitrogen supplied to the fungus.

In general the nitrogenous substances are both taken up and translocated but substances which are taken up by the mycelium and which are not translocated therein are effective in the preservation of food bases against infestation.

DETAILED DESCRIPTION OF THE INVENTION

The present invention is particularly applicable to the treatment of timber, including standing timber and tree stumps, whether the timber is infested or free from infestation, in which case the treatment is of course preservative. The control of dry rot fungi, in particular *Serpula lacrimans* and the control of *Armillaria mellea* (*Armillariella mellea*) and timber-infesting Basidiomycete is of particular interest.

The present invention may also find application for example in the treatment and preservation of lenses of cameras and other optical equipment over which fungi may spread destructively from a food base in the housing of the lens.

It will be appreciated that the suitability of a given substance for application can be ascertained by tests for whether the substance is non-metabolised and translocated within the mycelium of a particular fungus. Thus specimens of the fungus may be grown separately under otherwise identical conditions:

(a) in the absence of any nitrogen source
(b) in the absence of any nitrogen source other than the given substance, and
(c) in the presence of a sole recognised source of metabolisable nitrogen.

When the growth from (b) is identical to that from (a) and less than that from (c) the substance is non-metabolised and is suitable for use in the present method provided that translocation occurs within the mycelium. Translocation can be readily demonstrated by allowing uptake of the substance to take place at one region of the mycelium and by detecting the substance at a second region of the mycelium remote from the uptake region, e.g. by the use of sensitive analytical techniques such as chromatography.

The nitrogenous substance is suitably water soluble, non-toxic and non-corrosive and is preferably a non-metabolisable naturally occurring or synthetic amino acid (typically a non-protein amino acid) or a structural analogue of a naturally occurring amino acid, either in free form or in the form of a simple derivative such as a salt e.g. a salt of an alkali metal, usually of sodium or potassium or an acid salt. The molecular structures of such analogues, which generally act as metabolic inhibitors (i.e. antimetabolites or compounds which inhibit growth by competition for utilisable nitrogen at a growth point in the fungal mycelium) are usually derivable from those of naturally occurring amino acids by addition and/or replacement of a single group. Such a group generally consists of no more than 25 atoms and may for example be a $C_1$–$C_6$ alkyl group, an aromatic, e.g. an aryl group, a hydroxyl, sulphoxide, sulphonic acid, halogeno or nitro group. The substance may be a metabolic antagonist of glutamine or glutamic acid e.g. DL methionine sulphoxide, $CH_3SOCH_2CH_2CH(NH_2)CO_2H$ or e.g. δ-hydroxylysine HCl, $NH_2CH_2CH(OH)CH_2CH_2CH(NH_2)CO_2H\cdot HCl$ or of aspartic acid, alanine or glycine. The compound aminoisobutyric acid, $(CH_3)_2C(NH_2)CO_2H$, which is odourless, colourless and non-corrosive or the amine salt e.g. the hydrochloride or an alkali metal salt is particularly preferred especially when the growth of *S. lacrimans* is to be inhibited.

The nitrogenous substance is usually applied to the mycelium or the infested or uninfested food base as a paint or spray or, in the case of uninfested timber, by soaking the timber in a solution or dispersion of the substance in a liquid medium, which is preferably aqueous. It may be advantageous to mix the nitrogenous substance with an energy source, which is generally a carbohydrate and typically a sugar in order to promote uptake of the substance by the mycelium. Alternatively or additionally the nitrogenous substance may be mixed with one or more growth promoting agents, e.g. mineral sources, so as to increase the surface area of the mycelium exposed for treatment.

According to a further aspect of the present invention a composition for inhibiting the growth of a fungus capable of sustaining growth over a non-nutrient surface comprises a nitrogenous substance which is translocated within the mycelium of the fungus and which is not utilised by the fungus for growth when the substance is the sole source of nitrogen supplied to the fungus, the substance being combined together with one or both of (a) an energy source which promotes the uptake of the substance by the mycelium and (b) a growth-promoting agent which increases the surface area of the mycelium.

Suitable energy sources include for example monosaccharide or disaccharides such as sucrose, or polysaccharides such as cellulose, and suitable growth-promoting agents include flavonoids and minerals such as magnesium, potassium, iron, sulphates and phosphates e.g. $KH_2PO_4$. The nitrogenous substance generally amounts to no more than 10% and usually no more than 1% by weight of the composition applied, the energy source is generally present in a concentration no greater than 20%, although a concentration no greater than 10% is preferred and a concentration no greater than 3% typical. The concentration of the mineral source is usually no greater than 0.5% by weight.

Although generally applied when dissolved or dispersed in a liquid medium the nitrogenous substance may, in order to reduce transport and other costs, be packaged as a concentrate, e.g. as a powder either alone or mixed with one or more of an energy source and a growth promoting agent. The addition of a suitable quantity of solvent or dispersant which is usually water then produces a composition suitable for application.

The invention is illustrated by the following Examples:

EXAMPLE 1

Inhibition of growth of *S. lacrimans* by aminoisobutyric acid

Mycelium of *S. lacrimans* is allowed to grow radially from a disc of 1% malt agar over the dry surface of an otherwise empty petri dish. When the colony is 17.5 mm in diameter aminoisobutyric acid(AIB) is added to the agar at a concentration 10 wt%. The results are shown in Table 1 together with a control in which no AIB is added.

TABLE 1

| Time (weeks) | Colony diameter (No AIB) mm | Colony diameter (AIB added) mm |
|---|---|---|
| 0 | 18 | 17 |
| 1 | 35 | 18 |
| 2 | 43 | 18 |
| 3 | 50 | 18 |

EXAMPLE 2

Treatment of infested timber with AIB

Mycelium of *S. lacrimans* is established in wood blocks and allowed to grow out from them over a non-nutrient surface. An aqueous solution containing 100 mg/ml AIB is then added to the blocks (0.2 ml) causing inhibition of growth persisting for at least three months in the edge of the mycelium 10 cm from the point of application.

EXAMPLE 3

Effect of AIB in inhibiting spread of mycelium from a wood foodbase

The effect of addition of AIB to wood-based colonies of *S. lacrimans* is tested, using the same arrangement as in Example 1 but substituting a colonised wood block for the colonised agar disc placed centrally in an empty dish. After the mycelium has begun to spread from the wood across the base of the dish, 0.2 ml of AIB solution 100 mg/ml is added to half the plates.

Results

Growth increment (cm$^2$) in 7 months following addition of inhibition:

| Run | AIB-treated | Controls (no inhibitor) |
|---|---|---|
| 1 | 20.9 | 70.5 |
| 2 | 27.6 | 74.6 |
| 3 | 17.9 | 55.2 |

Percent area increase in 7 month period (cm$^2$):

| Run | AIB-treated | Controls (no inhibitor) |
|---|---|---|
| 1 | 37.6 | 65.9 |
| 2 | 40.9 | 59.0 |
| 3 | 34.3 | 50.4 |

It will be seen that AIB decreases the spread from a wood foodbase. Mycelium on treated blocks remains alive, but its rate of extension is decreased, showing that AIB affects growth at a distance from the point of application.

EXAMPLE 4

Effect of DL metionine sulphoxide (MS) in inhibiting spread of mycelium from an agar foodbase Mycelium of *S. lacrimans* is allowed to grow radially from discs of 1% malt agar over the dry surface of otherwise empty petri dishes. After seven days 0.05 ml of an aqueous solution of MS at a concentration 10 mg/ml$^{-1}$ is added to several discs whilst others remain untreated as controls.

The results are set out in Table 2:

TABLE 2

| No. of days after inoculation | Colony diameter (cm) treated | Colony diameter (cm) untreated |
|---|---|---|
| 7 | 22 | 22 |
| 9 | 17.4 | 24.4 |
| 13 | 18.1 | 26.2 |
| 15 | 19.1 | 27.8 |

EXAMPLE 5

A similar procedure to that in Example 4 is carried out except that the concentration of MS is increased to 240 mg/ml$^{-1}$. Twenty days after inoculation the average diameter of the treated colony is 21.7±1.5 cm whereas the average diameter of the untreated colony is 25±2.5 cm.

What is claimed as new and desired to be secured by Letters Patent of the United States is:

1. A composition, comprising:
   (a) a nitrogenous compound selected from a group consisting of DL methionine sulfoxide, δ-hydroxylysine.HCL, aminoisobutyric acid, alkali metal salts thereof, acid-addition salts thereof, and mixtures thereof, in an amount effective for inhibiting the growth of timber fungus; and
   (b) a second compound selected from the group consisting of monosaccharides, disaccharides, polysaccharides or mixtures thereof in an amount effective for promoting the uptake of the nitrogenous compound.

2. The composition of claim 1, wherein the amount of the nitrogenous compound is not in excess of 10% by weight.

3. The composition of claim 1, further comprising:
   (c) a suitable solvent or dispersant.

4. The composition of claim 3, wherein the solvent or dispersant is water.

5. A composition, comprising:
   (a) a nitrogenous compound selected from the group consisting of DL methionine sulfoxide, δ-hydroxylysine.HCl, aminoisobutyric acid, alkali metal salts thereof, acid-addition salts thereof, and mixtures thereof, in an amount effective for inhibiting the growth of timber fungus;

(b) a a growth-promoting compound selected from the group consisting of flavonoids, magnesium salts, potassium salts, iron salts, sulfate salts, phosphate salts and mixtures thereof, in an amount effective for promoting the growth of a timber fungus; and (c) a suitable solvent or dispersant.

6. The composition of claim 5, wherein the amount of nitrogenous compound is not in excess of 10% by weight.

7. The composition of claim 6, wherein the amount of salt is not in excess of 0.5% by weight.

8. The composition of claim 5, further comprising a third compound selected from the group consisting of monosaccharides, disaccharides, polysaccharides, or mixtures thereof in an amount effective for promoting the uptake of the nitrogenous compound by the fungus.

9. The composition of claim 8, wherein the disaccharide is sucrose.

10. The composition of claim 8, wherein the polysaccharide is cellulose.

11. The composition of claim 8 wherein the third compound is not in excess of 10% by weight.

12. A composition comprising:
a nitrogenous compound selected from the group consisting of DL methionine sulfoxide, δ-hydroxylysine.HCl, aminoisobutyric acid, alkali metal salts thereof, acid-addition salts thereof, and mixtures thereof, in an amount effective for inhibiting the growth of timber fungus; and
a growth-promoting compound selected from the group consisting of flavonoids, magnesium salts, potassium salts, iron salts, sulfate salts, phosphate salts, and mixtures thereof in an amount effective for promoting the growth of a timber fungus.

13. The composition of claim 12, further comprising:
a third compound selected from the group consisting of monosaccharides, disaccharides, polysaccharides, and mixtures thereof in an amount effective for promoting the uptake of the nitrogenous compound by the fungus.

14. A method of inhibiting the growth of timber fungus, which comprises applying to a timber substrate a composition comprising:
(a) a nitrogenous compound selected from the group, consisting of DL methionine sulfoxide, δ-hydroxylysine.HCl, aminoisobutyric acid, alkali metal salts thereof, acid-addition salts thereof, and mixtures thereof, in an amount effective for inhibiting the growth of said fungus; and
(b) a growth-promoting compound selected from the group consisting of flavonoids, magnesium salts, potassium salts, iron salts, sulfate salts, phosphate salts, and mixtures thereof, in an amount effective for promoting the growth of a timber fungus.

15. The method of claim 14, wherein the timber fungus is selected from the group consisting of *Serpula lacrimans, Armillaria mellea,* and a timber-infesting Basidiomycete.

16. The method of claim 14, wherein the compound used is DL methionine sulfoxide.

17. The method of claim 16, wherein the compound is aminoisobutyric acid, or an alkali metal salt thereof.

18. The method of claim 17, wherein the compound is δ-hydroxylysine.HCl.

19. The method of claim 14, wherein the amount of the nitrogenous compound is not in excess of 10% by weight.

20. The method of claim 19, wherein the amount of the nitrogenous compound is not in excess of 1% by weight.

21. The method of claim 14, wherein the application is carried out by spraying the composition on said timber substrate.

22. The method of claim 14, wherein the application is carried out by soaking said timber substrate in a solution or a dispersion of said composition in a liquid medium.

23. The method of claim 22, wherein the liquid medium is water.

24. The method of claim 14, wherein the application is carried out by painting said timber substrate with said composition.

25. A method of inhibiting the growth of timber fungus, which comprises applying to a timber substrate a composition comprising:
(a) a nitrogenous compound selected from the group, consisting of DL methionine sulfoxide, δ-hydroxylysine.HCl, aminoisobutyric acid, alkali metal salts thereof, acid-addition salts thereof, and mixtures thereof, in an amount effective for inhibiting the growth of said fungus; and
(b) a compound selected from the group consisting of monosaccharides, disaccharides, polysaccharides, and mixtures thereof in an amount effective for promoting the uptake of the nitrogenous compound by the fungus.

26. The method of claim 25, wherein the timber fungus is selected from the group consisting of *Serpula lacrimans, Armillaria mellea,* and a timber-infesting Basidiomycete.

27. The method of claim 25, wherein the compound used is DL methionine sulfoxide.

28. The method of claim 27, wherein the compound is aminoisobutyric acid, or an alkali metal salt thereof.

29. The method of claim 28, wherein the compound is δ-hydroxylysine.HCl.

30. The method of claim 19, wherein the amount of the nitrogenous compound is not in excess of 10% by weight.

31. The method of claim 30, wherein the amount of the nitrogenous compound is not in excess of 1% by weight.

32. The method of claim 25, wherein the application is carried out by spraying the composition on said timber substrate.

33. The method of claim 25, wherein the application is carried out by soaking said timber substrate in a solution or a dispersion of said composition in a liquid medium.

34. The method of claim 33, wherein the liquid medium is water.

35. The method of claim 25, wherein the application is carried out by painting said timber substrates with said composition.

* * * * *